(12) United States Patent
Hossainy et al.

(10) Patent No.: US 7,820,732 B2
(45) Date of Patent: Oct. 26, 2010

(54) METHODS FOR MODULATING THERMAL AND MECHANICAL PROPERTIES OF COATINGS ON IMPLANTABLE DEVICES

(75) Inventors: Syed Faiyaz Ahmed Hossainy, Fremont, CA (US); Yiwen Tang, San Jose, CA (US); Harshad Borgaonkor, San Jose, CA (US); Jessica Reneé DesNoyer, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1316 days.

(21) Appl. No.: 10/835,656

(22) Filed: Apr. 30, 2004

(65) Prior Publication Data

US 2005/0245637 A1    Nov. 3, 2005

(51) Int. Cl.
*A61F 2/00* (2006.01)
*A61L 31/06* (2006.01)
*A61L 31/10* (2006.01)
*A61L 27/18* (2006.01)

(52) U.S. Cl. ........................ 523/113; 424/422
(58) Field of Classification Search .................. 424/423
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,849,514 A | 11/1974 | Gray, Jr. et al. | 260/857 |
| 4,226,243 A | 10/1980 | Shalaby et al. | 128/335.5 |
| 4,304,767 A | 12/1981 | Heller et al. | |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,931,287 A | 6/1990 | Bae et al. | 424/484 |
| 4,941,870 A | 7/1990 | Okada et al. | 600/36 |

(Continued)

FOREIGN PATENT DOCUMENTS

DE    42 24 401    1/1994

(Continued)

OTHER PUBLICATIONS

Campbell, Ian M. Introduction to Synthetic Polymers. 1994; Oxford University Press. pp. 45-50.*

(Continued)

*Primary Examiner*—Sharmila Gollamudi Landau
*Assistant Examiner*—Rachael E Welter
(74) *Attorney, Agent, or Firm*—Squire, Sanders & Dempsey L.L.P.

(57) ABSTRACT

Methods for modulating and enhancing thermal and mechanical properties and biocompatibilities of coatings on implantable devices are disclosed. Implantable devices containing the enhanced thermal and mechanical properties and biocompatibilities are also described. The implantable devices can be used to treat a medical condition such as vulnerable plaque or restenosis.

3 Claims, 2 Drawing Sheets

U.S. PATENT DOCUMENTS

| | | | |
|---|---|---|---|
| 4,977,901 A | 12/1990 | Ofstead | 128/772 |
| 5,019,096 A | 5/1991 | Fox, Jr. et al. | 623/1 |
| 5,085,629 A * | 2/1992 | Goldberg et al. | 604/8 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,163,952 A | 11/1992 | Froix | 623/1 |
| 5,165,919 A | 11/1992 | Sasaki et al. | 424/488 |
| 5,219,980 A | 6/1993 | Swidler | 528/272 |
| 5,231,140 A * | 7/1993 | Kilburg et al. | 525/274 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,376,406 A * | 12/1994 | Asanuma et al. | 427/226 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,828 A * | 10/1995 | Moffat et al. | 430/109.3 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | 378/64 |
| 5,516,881 A | 5/1996 | Lee et al. | 528/320 |
| 5,569,463 A | 10/1996 | Helmus et al. | 424/426 |
| 5,578,073 A | 11/1996 | Haimovich et al. | 623/1 |
| 5,581,387 A | 12/1996 | Cahill | |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,644,020 A | 7/1997 | Timmermann et al. | 528/288 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,861,387 A | 1/1999 | Labrie et al. | |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,932,539 A * | 8/1999 | Stupp et al. | 514/2 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |

| Patent No. | Date | Inventor | Reference |
|---|---|---|---|
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 214/252.1 |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Castro et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,703,040 B2 | 3/2004 | Katsarava et al. | |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091230 A1 | 7/2002 | Mao et al. | |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0057601 A1* | 3/2003 | Reitz et al. | 264/239 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0203991 A1* | 10/2003 | Schottman et al. | 523/334 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |
| 2004/0170685 A1* | 9/2004 | Carpenter et al. | 424/468 |

| | | | |
|---|---|---|---|
| 2005/0048121 A1 * | 3/2005 | East et al. ............... | 424/486 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/32777 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/56376 | 9/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/066241 | 7/2005 |

OTHER PUBLICATIONS

Odian, George. Principles of Polymerization, 3rd ed. 1991; John Wiley & Sons. pp. 29-37.*

Hsu et al., The Influence of Aromatic Diols on Thermotropic Poly-(ester-amide)s Synthesized by Direct Polycondensation, Journal of Polymer Research, vol. 3, No. 2, pp. 89-95, Apr. 1996.*

Chung et al., Synthesis and Characterization of Wholly Aromatic Polyesters Derived from 1-Phenyl-2,6-naphthalene-dicarboxylic Acid and Aromatic Diols, Journal of Polymer Science: Part A: Polymer Chemistry, vol. 34, pp. 1105-1112, 1996.*

Larrain et al., Glass Transition Temperature-molecular Weight Relation for Poly(hexamethylene perchloroterephthalamide), Polymer Bulletin 4, pp. 487-490, 1981.*

Invitation to pay additional fees for PCT/US2005/014511, filed Apr. 27, 2005, 11 pgs.

International Search Report and Written Opinion for PCT/US2005/014511, filed Apr. 27, 2005, mailed Feb. 20, 2006, 27 pgs.

U.S. Appl. No. 10/718,278, filed Nov. 19, 2003, Hossainy et al.

U.S. Appl. No. 10/719,516, filed Nov. 21, 2003, Tang et al.

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.

De Lezo et al., *Intracoronary Ultrasound Assessment of Directional Coronary Atherectomy: Immediate and Follow-Up Findings*, JACC vol. 21, No. 2, (1993) pp. 298-307.

Moreno et al., *Macrophage Infiltration Predicts Restenosis After Coronary Intervention in Patients with Unstable Angina*, Circulation, vol. 94, No. 12, (1996) pp. 3098-3102.

Oikawa et al., Mechanisms of Acute Gain and Late Lumen Loss After Atherectomy in Different Preintervention Arterial Remodeling Patterns, *The Am. J. of Cardilogy*, vol. 89, (2002) pp. 505-510.

Scully et al., *Effect of a heparan sulphate with high affinity for antithrombin III upon inactivation of thrombin and coagulaton Factor Xa*, Biochem J. 262, (1989) pp. 651-658.

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

U.S. Appl. No. 10/630,250, filed Jul. 30, 2003, Pacetti et al.

U.S. Appl. No. 10/816,072, filed Mar. 21, 2004, Dugan et al.

U.S. Appl. No. 10/805,036, filed Mar. 16, 2004, Pacetti.

U.S. Appl. No. 10/738,704, filed Dec. 16, 2003, Pacetti et al.

U.S. Appl. No. 10/750,139, filed Dec. 30, 2003, DesNoyer et al.

U.S. Appl. No. 10/741,214, filed Dec. 19, 2003, Pacetti.

Anonymous, *Cardiologists Draw—Up the Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(a-amino acid)$\beta,\omega$-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Mark, *Physical Properties for Polymer Handbook*, 1996, pp. 147-149.

\* cited by examiner

METHODS FOR MODULATING THERMAL AND MECHANICAL PROPERTIES OF COATINGS ON IMPLANTABLE DEVICES

BACKGROUND OF THE INVENTION

1. Field of the Invention

This invention generally relates to a coating composition for coating implantable devices, such as a stent.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention, but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

Figure 1:
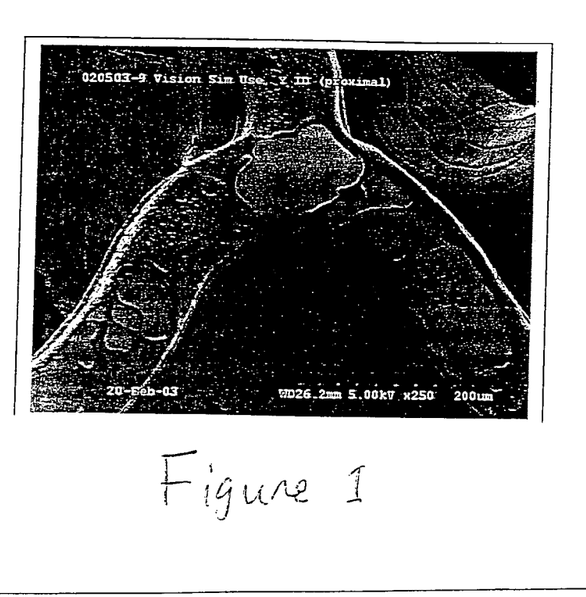
FIG. 1 is a SEM (scanning electron micrograph) of poly (ester amide benzyl ester) coated Vision™ stent, showing mechanical failure due to balloon shear.

The glass transition temperature ($T_g$) of a polymer plays an important role in defining coating characteristic. A coating material with a very low $T_g$ induces unacceptable rheological behavior upon mechanical perturbation such as crimping of the coated stent on a balloon as well as the sheer force exerted on the coated stent by balloon expansion and withdrawal. As used herein, the term "unacceptable rheological behavior" refers to the rheological behavior of the coating which is not suitable for use as a coating on a medical device such as a stent. On the other hand, a coating material with a high $T_g$ introduces brittle fracture in the high strain areas of the coating. FIG. 1 is a scanning electron micrograph of a poly(ester amide) benzyl ester coated small Vision stent (12 mm, available from Guidant Crop.) depicting the typical degree of damage observed post-expansion. Accordingly, the glass transition temperature of the polymer needs to be adjusted so as to provide suitable coating characteristics such that the coating is not too soft or too brittle. The adjustment in the glass transition temperature should be aimed at eliminating or significantly reducing coating damage caused by stent expansion, crimping or damage caused by the balloon.

The biocompatibility of the polymer, moreover, plays an important role in drug delivery stent technology. The coating should not provide for an adverse response so as to negate the affects of the drug on the stented lesion. Should the coating cause, for example, excessive inflammation, the feasibility of using the stent, despite is medicinal effects, is compromised. Accordingly, the coating should be inert or otherwise provide for a positive biological response.

The polymer used for the coating should also provide for control over delivery of a therapeutic agent. The coating should not release the agent too fast or the agent should not remain in the coating for an unacceptable period of time. If the drug is released too quickly, it may not provide an efficacious dose for an adequate duration of time. If the drug is released too slowly, it may not provide for an acceptable treatment regiment.

The various embodiment of the present invention address these and other needs.

SUMMARY OF THE INVENTION

A method of modulating thermal, mechanical, and surface properties of a coating on an implantable device comprising a polymer is provided. Also provided are a coating with enhanced thermal, mechanical and surface properties, a medical device comprising the coating and a method of using the medical device for treating a disorder such as restenosis and vulnerable plaque. The medical device can be, for example, a drug-delivery stent.

In one embodiment, where the coating comprises a polymer having a low Tg, the method comprises modifying the backbone, increasing the molecular weight, or narrowing the molecular weight distribution of the polymer to increase the Tg of the polymer. The backbone of the polymer can be modified by attaching, for example, a short chain diacid, an aromatic diol, an aromatic diacid, styrene, to the backbone. Alternatively, the polymer can be modified by replacing the pendant groups on the polymer with less bulky linear groups or more bulky groups that increase the potential rotation barrier of the polymer.

Where the coating comprises a polymer having a high Tg, the method comprises altering the polymer backbone, decreasing the molecular weight, or broadening the molecular weight distribution of the polymer to decrease the Tg of the polymer. The backbone of the polymer can be modified by attaching, for example, flexible blocks such as polyethers to the backbone. Alternatively, the polymer can be modified by replacing the pendant groups on the polymer with more bulky linear groups or less bulky groups that decrease the potential rotation barrier of the polymer.

In another embodiment, the coating comprising a polymer can be modified to include a hydrophilic, non-fouling polymer. Upon the coating development, the hydrophilic, non-fouling polymer segregates to the coating surface, resulting in improved in vivo biocompatibility of the coating.

In a further embodiment, the properties of a coating comprising a first, bulk polymer having a high $T_g$ can be improved by blending the first polymer with a second, minor polymer having a low $T_g$. Conversely, the properties of a coating comprising a first polymer that is the bulk polymer having a low $T_g$ can be improved by blending the first polymer with a second polymer that is the minor polymer having a high $T_g$. The coating can comprise about 50%-99.99% the bulk polymer and about 0.01%-50% the minor polymer.

In a further embodiment, the properties of a coating comprising a first polymer which is the bulk polymer that can have either a high or low $T_g$ can be improved by blending the first polymer with a second, minor polymer that is a semi-crystalline polymer having a very low $T_g$ and a melting point ($T_m$). The coating can comprise about 50%-99.99% the bulk polymer and about 0.01%-50% the minor polymer.

The mechanical properties of a coating on an implantable device can be improved by incorporating into the coating bioabsorbable or non-bioabsorable chopped fibers or high surface/volume ratio particulates to reinforce the coating.

The coatings disclosed herein with enhanced mechanical, thermal, and surface properties can further include a bioactive agent effective for treating a disease such as stenosis or cancer.

DETAILED DESCRIPTION

Method for Modulation of Surface Properties of Polymeric Coatings

A method of modulating thermal, mechanical, and surface properties of a coating on an implantable device including a polymer is provided. Also provided are a coating with enhanced thermal, mechanical and surface properties, a medical device including the coating and a method of using the medical device for treating a disorder such as restenosis and vulnerable plaque. The medical device can be, for example, a drug-delivery stent. A coating composition can be changed and then applied to a device or the polymer can be applied to the device and then modified.

Figure 2:
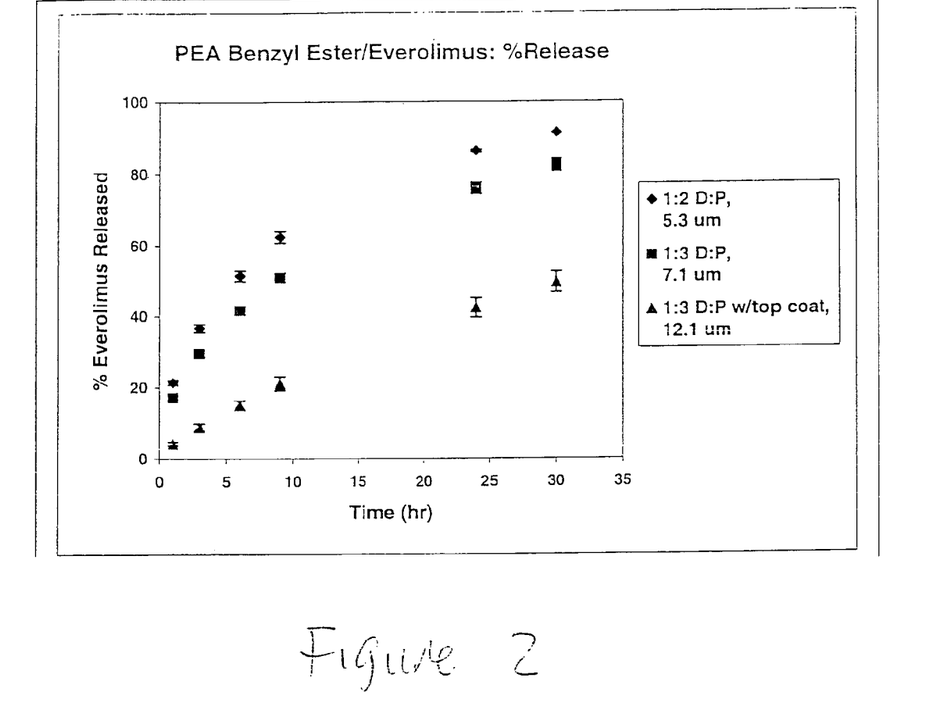
FIG. 2 is an in vitro percent release rate from PEA Benyl Ester/everolimus coated stents.

In one embodiment, if the coating including a polymer having a low $T_g$, the method comprises modifying the backbone, increasing the molecular weight, or narrowing the molecular weight distribution of the polymer to increase the $T_g$ of the polymer. Low $T_g$ materials have a proclivity to be softer and are more prone to failure during mechanical perturbations, such as crimping and balloon expansion. Additionally, low $T_g$ materials are more permeable to a drug such as everolimus and therefore, exhibit higher drug release rates e.g., poly (ester amide) as shown in FIG. 2). To improve the mechanical properties of a coating formed of a low $T_g$ polymer, the backbone of the polymer can be modified by attaching, for example, a short chain diacid, an aromatic diol, an aromatic diacid, or styrene, to the backbone. Alternatively, the polymer can be modified by replacing more bulky linear pendant groups on the polymer with less bulky linear groups so as to reduce the fractional free volume. In yet other embodiments, side groups that interfere with rotational motion of the polymer can be added to increase $T_g$. However, bulky side groups that inhibit rotation also increase fractional free volume of the polymer, which may decrease $T_g$.

If the coating including a polymer having a high $T_g$, the method comprises altering the polymer backbone, decreasing the molecular weight, or broadening the molecular weight distribution of the polymer to decrease the $T_g$ of the polymer. The backbone of the polymer can be modified by attaching, for example, flexible blocks such as polyethers to the backbone. Alternatively, the polymer can be modified by replacing less bulky linear pendant groups on the polymer with more bulky linear groups so as to increase the fractional free volume to decrease $T_g$. In yet other embodiments, side groups that generate less interference with rotational motion of the polymer can be added to decrease $T_g$. However, side groups that generate less interference with rotational motion of the polymer also decrease fractional free volume of the polymer, which may increase $T_g$.

In another embodiment, the coating including a polymer (e.g., polyester amide) can be modified to include a hydrophilic, non-fouling polymer. Upon the coating development, the hydrophilic, non-fouling polymer segregates to the coating surface, resulting in improved in vivo biocompatibility of the coating.

In a further embodiment, the properties of a first, bulk polymer having a high $T_g$ can be improved by blending the first polymer with a second, minor polymer having a low $T_g$. Conversely, the properties of a first polymer that is the bulk polymer having a low $T_g$ can be improved by blending the first polymer with a second polymer that is the minor polymer having a high $T_g$. The coating can have about more than 50%-99.99% the bulk polymer and about 0.01%-less than 50% the minor polymer.

In a further embodiment, the properties of a coating comprising a first polymer which is the bulk polymer that can have either a high or low $T_g$ can be improved by blending the first polymer with a second, minor polymer that is a semi-crystalline polymer having a very low $T_g$ and/or a melting point ($T_m$). The coating can comprise about 50%-99.99% the bulk polymer and about 0.01%-50% the minor polymer.

In some embodiments, a filling material can be combined with the coating. The filling materials can be, for example, high surface to volume ratio (S/V) chopped fibers from absorbable or non-absorbable polymers, high surface to volume ratio (S/V) inert or bioactive particulates. Generally, useful filling materials have a surface to volume ration in the range between 1% and 50%, for example. The filling material comprises about 0.01%-50%, e.g., about 1%-20%, or about 1%-10% of the total coating composition.

The polymeric coating with modified mechanical or surface properties may optionally include a bioactive agent for controlled delivery of the agent. The composition can be used for coating an implantable device such as a stent.

As used herein, the term "low $T_g$ polymer" refers to a biocompatible polymer having a glass transition temperature below about body temperature (37° C. for human beings). The term "high $T_g$ polymer" refers to a biocompatible polymer having a glass transition temperature above about the body temperature. The term "very low $T_g$" refers to a $T_g$ about 20° C. below the body temperature, for example, about 25° C., 30° C., 35° C., 40° C., 45° C., 50° C., or 55° C. below the body temperature.

$T_g$ as used herein generally refers to the temperature at which the amorphous domains of a polymer change from a brittle vitreous state to a plastic state at atmospheric pressure. In other words, $T_g$ corresponds to the temperature where the onset of segmental motion in the chains of the polymer occurs, and it is discernible in a heat-capacity-versus-temperature graph for a polymer. When an amorphous or semicrystalline polymer is heated, its coefficient of expansion and heat capacity both increase as the temperature rises, indicating increased molecular motion. As the temperature rises, the sample's actual molecular volume remains constant. Therefore, a higher coefficient of expansion points to a free volume increase of the system and increased freedom of movement for the molecules. The increasing heat capacity corresponds to increasing heat dissipation through movement.

$T_g$ of a given polymer can be dependent on the heating rate and can be influenced by the thermal history of the polymer. Furthermore, polymer chemical structure heavily influences $T_g$ by affecting polymer mobility. $T_g$ of a polymer increases along with the increase of the rotational barrier of the polymer. $T_g$ of a polymer decreases along if the fractional free volume of the polymer increases. As discussed above, bulky pendant groups tend to inhibit rotational motion of a polymer but increase fractional free volume of the polymer. Therefore, generally, flexible main-chain components lower $T_g$ and side groups that inhibit or interfere with rotational motion of the polymer raise $T_g$. Conversely, increasing flexible-side-group length of a polymer increases fractional free volume of the polymer and thus lowers $T_g$. Generally, increasing main-chain polarity increases $T_g$.

For example, Tg can be increased by the following architecture changes: (1) increase in chain stiffness resulting from longer, rigid units in the backbone, (2) potential barriers to rotation resulting from more bulky, side groups (e.g., PMMA and PMA), (3) increasing the interactions between neighboring polymer chains by incorporating ionic and H-bonding groups in the side chain (see, for example, polypropylene (PP) (−14° C.) vs. polyacrylonite (PAN) (103° C.), and (4) increasing the asymmetry and thereby increasing the dipole interaction (see, for example, polyisobutylene (PIB) (−73° C.) vs. PP (−14° C.)) (James E. Mark; Physical properties for Polymer Handbook; 1996; Page 147-149). On the other hand, the increase in linear side chains may decrease the Tg by increasing fractional free volume. For example, the poly(n-butyl methacrylate) (PBMA) (29° C.) has a lower Tg than polymethyl Methacrylate (PMMA) (100° C.) (James E. Mark; Physical properties for Polymer Handbook; 1996; Page 147-149).

Additionally, the presence of crosslinks can increase the observed $T_g$ for a given polymer, and the presence of a drug or therapeutic agent can alter the $T_g$ of a polymer due to plasticization effects. The magnitude of these plasticization effects depends on the miscibility and compatibility of the drug and polymer and the loading of drug in the polymer. Increasing the molecular weight and/or narrowing the range of the molecular weight distribution of a polymer can also increase the $T_g$ of the polymer. Conversely, decreasing the molecular weight and/or broadening the range of the molecular weight of a polymer decrease the $T_g$ of the polymer.

It is recognized in the art that hydration of the molecule of a polymer may increase the glass transition temperature of the polymer. The glass transition temperature described herein refers to the glass transition temperature of the hydrated polymer when a coating formed therefrom is implanted within the body of an animal.

Modifying the Backbone

In accordance with a further aspect of the invention, the properties of a coating including a polymer having a low glass transition temperature ($T_g$) can be enhanced by modifying the backbone of the polymer to increase the $T_g$. To modify the backbone of the polymer, the polymer can be subjected to modification with a chemical agent to increase the regularity of the structure of the polymeric molecule. For example, low $T_g$ polymers having one or more functional groups such as COOH, OH, or an aromatic ring structure in the backbone can be modified with one or more stiffening groups such as short chain diacids, aromatic diols, aromatic diacids, or styrene so as to increase the glass-transition temperature of the polymer. The term "short chain diacids" refers to diacids having C1-C10 carbons. Some representative stiffening groups are given below:

To illustrate, poly(ester amide) (PEA), which has a low $T_g$ and has a COOH group in its backbone, can be modified with a stiffening group such as styrene, amide linkages, etc. (Scheme 1).

As another example, polymers having hydroxyl end groups can be modified by short chain diacids or aromatic diacids via an ester bond. Alternatively, polymers having hydroxyl end groups can be converted to other groups such as amino or aldehyde groups for further modification. One such polymer is PEG. Some representative PEG bearing various kinds of end groups are listed below:

The PEG bearing hydroxyl or amino end groups can be modified with a diacid, forming ester or amide bonds. The PEG bearing aldehyde end groups can be modified with stiffening groups having diamines (Scheme 2).

Methods of modifying the backbone of a low $T_g$ polymer have been well documented in the art (see, for example, Michael Smith, Organic Synthesis, $2^{nd}$ Edition, McGraw-Hill, 2001). For example, for backbones of low $T_g$ polymers bearing functional groups such as COOH, $SO_3H$ or other acidic or basic groups, poly(ester amide) being an example, stiffening pendant groups such as styrene, or amide linkages can be readily attached to the backbone so as to increase the $T_g$ of the low $T_g$ polymer.

The backbone of the low $T_g$ polymer can also be modified by replacing all or part of the pendant groups with different pendant groups such as less bulky pendant groups. As described above, fractional free volume and rotational barrier properties of a side chain can be counter active forces. In other words, more bulky side groups can increase the fractional free volume which may in effect increase rotational barrier effects of the side group, and inhibition of rotation can increase $T_g$. The increase of size in linear side chains may decrease the Tg by increasing fractional free volume (James E. Mark; Physical properties for Polymer Handbook; 1996; Page 147-149).

Formula I

Formula II

The $T_g$ of the modified polymer may be increased as the less linear bulky pendant groups would allow the polymer molecules to pack better. For example, the bulky pendant groups of a PEA of the structure of formula I can be replaced with less bulky groups such as H to yield a PEA having the structure of formula II. The PEA of formula II would have an increased $T_g$ as compared to the PEA of formula I.

Modifying the Molecular Weight

In accordance with another aspect of the invention, the glass transition temperature of a low $T_g$ polymer can be modified by increasing or decreasing the molecular weight of the polymer.

In one embodiment, the $T_g$ can be increased by increasing the molecular weight beyond the threshold of chain entanglement of the polymer. Chain entanglement refers to the phenomenon that polymer molecules entangle with one another as a result of the length of the molecules. Chain entanglement occurs because polymers are chain molecules that are characterized by a molecular length that is much greater than the other dimensions of the molecule. Since the bonding in the chain direction is covalent, and the bonding between chains is weak, polymers can exhibit highly anisotropic properties. Polymeric material will also exhibit isotropic properties when the chain segments are oriented randomly within the material. If the random orientation occurs down to a molecular length scale, the material becomes amorphous. Most amorphous polymers have chains that are long enough for them to entangle with one another. The molecular weight required for chain entanglement to occur is referred to as the critical molecular weight for a particular polymer. Therefore, increasing the length of a polymer molecule, which increases the molecular weight of the polymer, increases the glass transition temperature of the polymer.

Conversely, to decrease the $T_g$ of a polymer, one can decrease the molecular weight of the polymer.

In a further embodiment of the invention, the glass transition temperature of a low $T_g$ polymer can be increased by narrowing the molecular distribution of the polymer. A narrower distribution of polymer allows the polymer to have better packing and thus a higher glass transition temperature. Conversely, where a lower $T_g$ is desirable, one can select a polymer having a broader range of molecular weight distribution. For example, PolyAspirin in different grades has different molecular weight distribution pattern and has different glass transition temperatures (i.e., PolyAspirin 510, $M_w$, 20,000, $T_g$ 45° C.; PolyAspirin 261, $M_w$, 20,000 $T_g$ 35° C.; PolyAspirin 749, $M_w$, 20,000 $T_g$ 17° C.).

Blending in A Hydrophilic, Non-Fouling Polymer

In accordance with a further aspect of the invention, the properties of a polymeric coating including a coating polymer, which can be a hydrophobic polymer or can include a hydrophobic component, can be modified by incorporating into the coating one or more hydrophilic, blood compatible, non-fouling polymers. As mentioned before, the hydrophobic compound can be added before the composition is applied or subsequent to the application of the coating composition. The hydrophilic, non-fouling polymer can enhance the surface biocompatibility of a coating in that, after a coating process such as spray coating, but prior to implantation in a patient, the preferred energy conformation will drive the hydrophobic component of the composition to be enriched in the coating surface, and prior and/or subsequent to implantation in a patient, the hydrophilic, non-fouling polymer will segregate to the coating-air surface, resulting in improved biocompatibility in vivo of the coating.

Blending in the coating a hydrophilic, non-fouling polymer may also achieve multiple effects on the coating. In addition to the enhanced biocompatibility, a low $T_g$ hydrophilic, non-fouling polymer can reduce the effective $T_g$ of a coating comprising a high $T_g$ polymer, thereby improving mechanical properties of the coating. The hydrophilicity of the non-fouling polymer may also increase water uptake of the coating, thus increasing the drug release rate and possibly absorption rate of the coating.

As used herein, the term "hydrophobic" refers to an attribute of a material that defines the degree of water affinity of the molecules of the material. Hydrophobicity and hydrophilicity are relative terms. Generally, hydrophobicity and hydrophilicity of a polymer can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

If a blend of a hydrophobic and hydrophilic polymer(s) is used, whichever polymer in the blend has lower δ value compared to the δ value of the other polymer in the blend is designated as a hydrophobic polymer, and the polymer with higher δ value is designated as a hydrophilic polymer. If more than two polymers are used in the blend, then each can be ranked in order of its δ value. For the practice of the present invention, the value of δ of a particular polymer is inconsequential for classifying a polymer as hydrophobic or hydrophilic. For example, if the coating polymer is a PEA, a polymer having a δ value higher than that of PEA is designated as hydrophilic.

Various ratios of the coating polymer over the hydrophilic, non-fouling polymer can be selected. For example, the coating can have a ratio of the coating polymer over the hydrophilic, non-fouling polymer in the range between about 0.01/99.99 and about 99.99/0.01, for example, about 0.01/99.99, 0.1/99.9, 1/99, 5/95, 10/90, 25/75, 50/50, 75/25, 90/10, 95/5, 99/1, 99.9/0.1 and 99.99/0.01.

As used herein, the hydrophilic, non-fouling polymer useful in the composition disclosed herein includes both biodegradable and non-biodegradable polymers. Representative hydrophilic, non-fouling polymers include, but not limited to, poly(ethylene glycol) (PEG), poly(ethylene oxide), poly(ethylene glycol-co-propylene oxide) (PEG-PPO), dextran, dextrin, poly(vinyl alcohol), poly(2-hydroxyethyl)methacrylate (HEMA), polyvinylpyrrolidone (PVP), poly(butyleneterephthalate-co-ethylene glycol) (PBT-PEG or POLYACTIVE™), polyalkylene oxalates, pluronic acid, sulfonated polystyrene, block copolymers with a bioabsorbable block and a perfluoro chain, PEG-caprolactone, PEG-D,L-lactide, cellulosics, biomolecules such as fibrin, fibrinogen, cellulose, starch, collagen, heparin and hyaluronic acid, polyvinyl alcohols, and a combination thereof. In some embodiments, the hydrophilic, non-fouling polymer could exclude any one of these polymers. PEA can be combined with any particular one or combinations of these polymers.

Non-fouling is defined as preventing, delaying or reducing the amount of formation of protein build-up caused by the body's reaction to foreign material.

Theoretically, any hydrophilic, non-fouling polymer is useful in the disclosed composition. However, there is a tendency for the hydrophilic polymer component to leach out of the coating matrix. To minimize this tendency, one can choose a hydrophilic, non-fouling polymer having a molecular weight sufficiently high so as to not leach out of the composition. Generally, under physiological conditions, hydrophilic polymers leach out much easier from the coating. Therefore, the proper molecular weight of the polymer for coating the stent can be selected based on the hydrophilicity of the polymer—the more hydrophilic the polymer, the higher the molecular weight that one would need to choose to keep the polymer in the coating matrix.

Nonetheless, increasing the molecular weight of a hydrophilic polymer may decrease the polymer's ability to diffuse within the coating matrix. This may generate an adverse effect on surface blooming of the coating matrix. To minimize this effect, the molecular weight of the hydrophilic, non-fouling polymer can be below a critical molecular weight such that the hydrophilic, non-fouling polymer would retain its ability to diffuse readily within the coating matrix to allow surface blooming. As used herein, the critical molecular weight of a hydrophilic, non-fouling polymer generally refers to the maximum molecular weight at which the polymer retains its ability to diffuse.

Moreover, the proper molecular weight that one can select may also depend on the degradability of the hydrophilic, non-fouling polymer. For non-degradable, hydrophilic, non-fouling polymers, the proper molecular weight can be selected such that the polymeric molecule readily passes through the renal system. Typically, the proper molecular weight for a non-degradable, hydrophilic, non-fouling polymer would be below about 200,000 Daltons. For biodegradable hydrophilic, non-fouling polymers, larger molecules can be used because under physiological conditions, the biodegradable hydrophilic, non-fouling polymers can break down to smaller fragments and species that can readily pass through the renal system. Typically, the proper molecular weight for a degradable, hydrophilic, non-fouling polymer can be up to several million Daltons, e.g., 3 million Daltons.

Accordingly, the proper molecular weight would be one within the range between about the minimum molecular weight that a hydrophilic, non-fouling polymer would remain in the coating matrix and about the critical molecular weight of the polymer. In addition, the molecules of the polymer should be readily capable of passing through the renal system or breaking down into smaller fragments or species that can readily pass through the renal system. For example, a molecular weight of hyaluronic acid useful for forming the coating described herein would have a molecular weight between about 300,000 Daltons and about 2 millions Daltons, inclusive, and that of PEG would be between about 10,000 Daltons and about 150,000 Daltons, inclusive. For a poly(ester amide), the proper molecular weight can be one between about 50,000 Daltons and about 300,000 Daltons, for example, 150,000 Daltons.

Coating Polymers

The coating polymers that are modified can be any biocompatible low $T_g$ or high $T_g$ polymers. The coating polymer can be an absorbable or non-absorbable polymer. Absorbable is inclusive of bioerodable and biodegradable.

In one embodiment, the coating polymers can be any of the following: polyhydroxyalkanoates (PHA), poly(3-hydroxybutyrate) (PHB), poly(3-hydroxyvalerate) (PHV), poly(hydroxybutyrate-co-valerate), poly (ortho ester), polyanhydride, poly(D,L-lactide), poly(L-lactide), polyglycolide, poly(lactide-co-glycolide), poly(glycolic acid-co-trimethylene carbonate), polyphosphoester, polyphosphazenes, polyphosphoester urethane, poly(amino acids), poly(cyanoacrylates), poly(trimethylene carbonate), poly(iminocarbonate), polyurethanes, silicones, polyesters, polyolefins, polystyrene, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers with each other and olefins such as poly(butylenes-co-methacrylate) (PBMA) and ethylene-methyl methacrylate copolymers, acrylonitrile-styrene copolymers, block copolymers formed of a bioabsorbable block and a perfluoro chain, ABS resins, and ethylene-vinyl acetate copolymers, polyamides, such as Nylon 66 and polycaprolactam, alkyd resins, polycarbonates, polyoxymethylenes, polyimides, polyethers, epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

In another embodiment, the coating polymer can be a polymer having low $T_g$. Exemplary polymers having a low $T_g$ include, but are not limited to, poly(ester amide), poly(glycerol sebacic acid) (PGS), and low $T_g$ PolyAspirin. PolyAspirin is a drug having about 100 individual molecules of aspirin strung together in a chain to form an elastic compound, or polymer.

Blending A High $T_g$ Polymer with a Low Tg Polymer

In a further aspect of the present invention, the properties of a coating comprising a first, bulk polymer having a high $T_g$ can be improved by blending the first polymer with a second, minor polymer having a low or very low $T_g$. Conversely, the properties of a coating comprising a first polymer that is the bulk polymer having a low or very low $T_g$ can be improved by blending the first polymer with a second polymer that is the minor polymer having a high $T_g$. In some embodiments, bulk is the majority component of the blend. The coating can comprise about 50%-99.99% the bulk polymer and about 0.01%-50% the minor polymer. The resultant polymer blend would have an effective $T_g$ below the high $T_g$ and above the low $T_g$ or very low $T_g$. The effective $T_g$ of the polymer blend is the sum of the product of the molar ratio of the high $T_g$ polymer times the high $T_g$ plus the product of the molar ratio of the low $T_g$ polymer times the low $T_g$ ($T_{g(mix)} = N \times T_{g(high)} + (1-N) \times T_{g(low)}$).

Figure 4:
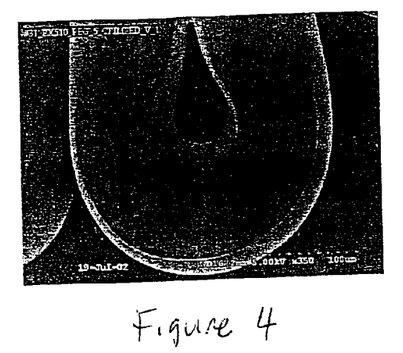
FIG. 4 is a SEM for crimped stent coated with 95% PolyAspirin (PX 510) mixed with 5% PEG (18.5K).
Figure 6:
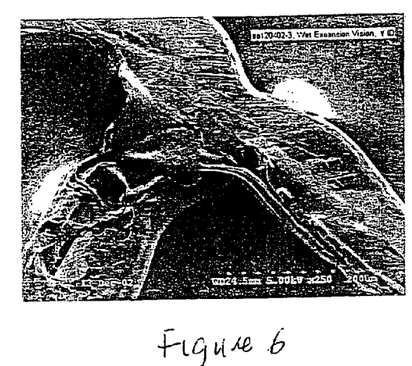
FIG. 6 is a SEM for wet expanded stent coated with poly (ester amide) (PEA) ($M_n$=44K, $T_g$ 16° C.).
Figure 8:
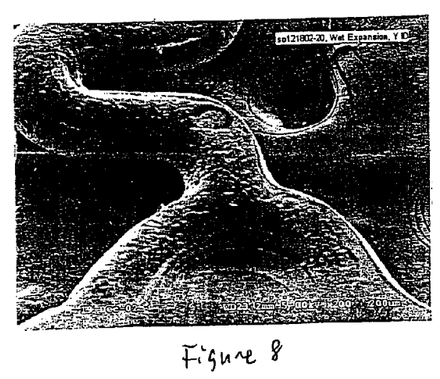
FIG. 8 is a SEM image of a stent coated with a composition containing a 300 μg mixture of poly(ester amide) (210 μg, $M_n$=44K, $T_g$=16° C.) and polycaprolactone (90 μg, inherent viscosity (i.v.) 1.14 dL/g, $T_m$ 60° C.) in a concentration of 2% (w/w) in a solvent mixture of tetrahydrofuran (THF) (68.6%) and DMAC (29.4%) (total 98%) and then dried at about 80° C. for 60 minutes in an oven.

Blending a low or very low $T_g$ polymer and a high $T_g$ polymer allows one to combine the mechanical strength of the high $T_g$ polymer and the flexibility of the low or very low $T_g$ polymer and thus to modulate the glass or melting temperature of a polymeric coating material and thus to control the mechanical properties of the coating. As shown in FIGS. 4, 6 and 8, implantable device coatings formed by a composition comprising a low $T_g$ polymer and a high $T_g$ polymer have good surface and mechanical properties. In addition, increasing the effective $T_g$ of the polymeric coating composition will also slow the release rate of a bioactive agent, if the composition includes an agent. Further, increasing the effective $T_g$ of the polymeric coating composition will slow the degradation rate of the composition, thereby reducing incidents of inflammatory responses to the degradation products released from polymer degradation.

In some embodiment, whether a polymer should be categorized as high $T_g$ or low $T_g$ is relative. The one having a higher $T_g$ is referred to as "high $T_g$ polymer", and the one having a lower $T_g$ is referred to as "low $T_g$ polymer." If more than one polymer is used, the polymers can be ranked in order of their respective $T_g$. The difference between the high and low $T_g$ should be of sufficient differences to achieve desired coating properties.

The high $T_g$ polymer is biocompatible, preferably, bioabsorbable. When the low $T_g$ polymer in the coating composition is a bioabsorable polymer, the high $T_g$ polymer is preferably a bioabsorbable polymer. Representative biocompatible, bioabsorbable polymers useful for the compositions disclosed herein include, but are not limited to, polyalkanoates (PHA), poly(3-hydroxyalkanoates) such as poly(3-hydroxypropanoate), poly(3-hydroxybutyrate) (PHB), poly(3-hydroxyvalerate) (PHV), poly(3-hydroxybutyrate-co-3-hydroxyvalerate) (PHBV), poly(3-hydroxyhexanoate), poly(3-hydroxyheptanoate) and poly(3-hydroxyoctanoate), poly(4-hydroxyalknaote) such as poly(4-hydroxybutyrate), poly(4-hydroxyvalerate), poly(4-hydroxyhexanote), poly(4-hydroxyheptanoate), poly(4-hydroxyoctanoate) and copolymers comprising any of the 3-hydroxyalkanoate or 4-hydroxyalkanoate monomers described herein or blends thereof, polyesters, poly(D,L-lactide), poly(L-lactide), polyglycolide, poly(lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(phosphoesters), poly(phosphazenes), poly(amino acids), polysaccharides, collagen, chitosan, alginate, PolyAspirin, and combinations thereof. As for blending with PEA, it is preferred that the minor component be miscible with PEA and have a higher $T_g$ than PEA.

Representative biocompatible, but non-bioabsorbable polymers include, but are not limited to, polyethers, polyamides, polyurethanes, polyalkylenes, polystyrene, poly(vinyl pyrrolidone) (PVP), alkylene vinyl acetate copolymers such as ethylene vinyl acetate (EVA), alkylene vinyl alcohol copolymers such as ethylene vinyl alcohol (EVOH or EVAL), and a combination thereof.

Representative low $T_g$ polymers useful for the polymeric coatings described herein include, but not limited to, poly(ester amide), polyglycerol sebacic acid (PGS), polyalkylene oxides, polyethylene glycol (PEG), polyethylene oxide, polypropylene oxide (PPO), poly(ethylene glycol-co-propylene oxide) (PEG-PPO), low $T_g$ PolyAspirin, low molecular weight DLPLA, and a combination thereof.

The term "low molecular weight DLPLA" refers to DLPLA having a molecular weight, for example, in the range between about 10,000 Daltons and about 20,000 Daltons. Low molecular weight DLPLA has a higher concentration of end-group, which can be —COOH or —OH, depending on the initiating species, typically a carboxylic acid or an alcohol, of the polymerization process making the PLA. Blending low molecular weight DLPLA in the coating would allow increase the concentration of —COOH or —OH end group in the polymer coating, which may increase water uptake, thereby having a better plasticizing effect and thus further decreasing the $T_g$. Therefore, blending low molecular weight DLPLA in the coating would have a double effect on the reduction of $T_g$. In addition, a higher concentration of the —COOH and/or —OH in the coating increases the release rate of a hydrophilic drug and also the absorption rate of an absorbable coating polymer. This is especially useful when the coating comprises a polymer that has a low in vivo degradation rate when it is desirable to enhance the degradation rate of the polymer. Examples of polymers having a low in vivo degradation rate include, but are not limited to PHB, PHBV, and DLPLA having a molecular weight more than 20,000 Daltons, etc.

Various ratios of the bulk low $T_g$ polymer over the minor high $T_g$ polymer can be selected. For example, the coating can have a ratio of the low $T_g$ polymer over the high $T_g$ polymer in the range between about 50/50 and about 99.99/0.01, for example, about 55/45, 60/40, 65/35, 70/30, 75/25, 80/20, 85/15, 90/10, 95/5, 99/1, 99.9/0.1 and 99.99/0.01.

Blending in a Semi-Crystalline Polymer

In a further aspect of the invention, the properties of a coating comprising a first polymer which is the bulk polymer that can have either a high or low $T_g$ can be improved by blending the first polymer with a second, minor polymer that is a semi-crystalline polymer having a very low $T_g$ and/or a melting point ($T_m$). The coating can comprise about 50%-99.99% the bulk polymer and about 0.01%-50% the minor polymer. For example, the ratio of the bulk polymer over the semi-crystalline polymer can be about 55/45, 60/40, 65/35, 70/30, 75/25, 80/20, 85/15, 90/10, 95/5, 99/1, 99.9/0.1 and 99.99/0.01.

Semi-crystalline materials such as polyamides generally do not exhibit a clear $T_g$ or 'rubbery' region. For these polymers the main transition occurs at $T_m$ when the crystalline regions break down. Some chain rotation in the amorphous regions will occur below $T_m$, giving some impact resistance at these temperatures. The inclusion of the $T_m$ contributes to the overall mechanical property of the coating.

Representative semi-crystalline polymers with a low or very low $T_g$ include high density polyethylene (HDPE), polycaprolactone (PCL), polypropylene, natural rubber (NR), polydimethyl siloxane (PDMS), polyethylene terephthalate (PET), nylon 6, polyetherimide (PEI), polytetrafluoroethylene (PTFE), polyvinylidene fluoride (PVDF), polyhexafluoropropylene (HFP), and a combination thereof.

Biocompatible Fillers

The polymeric coating with enhanced mechanical or surface properties disclosed herein can further include materials such as chopped fiber and high surface/volume (S/V) ratio particulates as reinforcements within the coating. As used herein, the term "high surface/volume ratio" refers to nano and/or microparticulates having a size in the range between 1 nanometer to 1000 microns, for example, particles of a size of about 10 nanometers, about 50 nanometers, about 100 nanometers, about 1 micron, about 10 microns, about 50 microns, about 100 microns, or about 200 microns.

Any biocompatible chopped fibers can be used. Representative useful chopped fibers include, but are not limited to, absorbable materials such as poly(glycolic acid), poly(dioxanone), absorbable glass fibers, carbon nanotube fibers and non-absorbable materials such as polyethylene (PE), poly (ethylene vinyl alcohol) (EVAL), polypropylene (PP), polyethylenetelephthalate (PET), hydroxyapatite, and combinations thereof. Exemplary useful high S/V particulates include, but are not limited to, alumina particulates, carbon nanoparticles, carbon nanoshells, carbon nanotubes, hydroxyapatite, tricalcium phosphate (TCP), carbides, nitrides, $TiO_2$, $SiO_2$, calcium sulfate, α-tricalcium phosphate (TCP), β-tricalcium phosphate (TCP), Carbonate-apatite (Dahlite), titanium (Ti), niobium (Nb), tantalum (Ta), platinum (Pt), alloy of platinum and iridium (Ir) (Pt/Ir), and combination thereof. It is noteworthy that some of the reinforcement materials, for example carbon nanotube, $Al_2O_3$, and polypropylene, may additionally contribute to passivation of the coating surface.

The chopped fibers and/or high S/V particulates can be present in the coating in various percentages, ranging, for example, from about 0.01% to about 20% of the total coating composition. In one embodiment, the coating can have about 1 wt %, about 5 wt %, or about 10 wt % of chopped fibers and/or high S/V particulates.

Bioactive Agents

The polymeric coatings described herein may optionally include one or more bioactive agents. The bioactive agent can be any agent which is biologically active, for example, a therapeutic, prophylactic, or diagnostic agent.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect for the patient. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, proteins, peptides, anti-inflammatory agents, antivirals, anticancer drugs, anticoagulant agents, free radical scavengers, estradiol, steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2- hydroxy)ethoxy]ethyl-rapamycin, and 40-O-tetrazole-rapamycin, ABT-578 (zotarolimus), clobetasol, cytostatic agents, prodrugs thereof, co-drugs thereof, and a combination thereof.

The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate including those that can be implanted in a human or veterinary patient. Examples of medical devices include, but not limited to, self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. For example, the device can be a bioabsorbable or bioerodable stent.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data do not limit the scope of the embodiments of the invention.

Example 1

Figure 3:
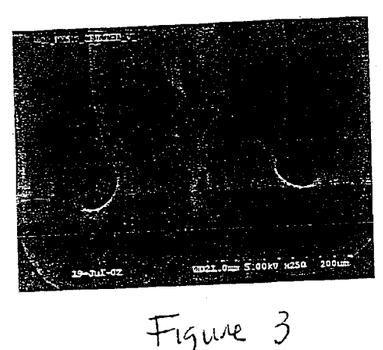
FIG. 3 is a SEM for crimped stent coated with PolyAspirin (PX510, $T_g$ 45° C.).

PENTA™ 13 mm stents (available from Guidant Corp.) were coated as described in the following:

A composition containing 400 µg PolyAspirin PX510 (Tg 45° C.) in a concentration of 2% (w/w) in chloroform was sprayed onto one stent. Each stent was rotated about the stent's central longitudinal axis at a speed of 3 rpm during coating. After a waiting period of 1 second following the application of the composition, warm air of approximately 80° C. was directed from an air gun onto each stent for 15 seconds to remove most of the solvent. The coated stent was dried for about 45 minutes in an oven at about 80° C. The stent was then subject to a crimp test. An SEM image of the coated stent is shown in FIG. 3.

Example 2

PENTA™ 13 mm stents were coated as described in the following:

The PENTA™ stents were coated with a composition containing a 400 µg mixture of high Tg PolyAspirin PX510 (PA) (Tg=45° C.) and PEG (Mw 18.5K) (Tg=−0.41° C.) (PolyAspirin:PEG=19/1 w/w) in a total concentration of 2% (w/w) in chloroform and then dried at about 80° C. for 45 minutes in an oven. The Tg of the coating of this polymeric mixture (Tg mix) is 40.7° C. (Tg mix=5% Tg PEG+95% Tg PA=40.7° C.) The stents were then subject to a crimp test. An SEM image of the coated stent is shown in FIG. 4.

Example 3

Figure 5:
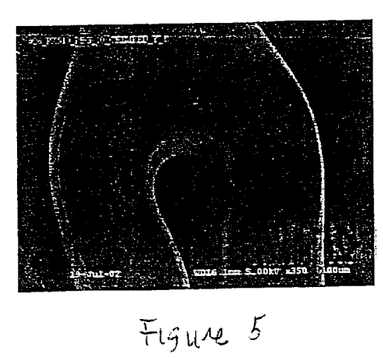
FIG. 5 is a SEM for crimped stent coated with 90% PolyAspirin (PX510) mixed with 10% PEG (18.5K).

PENTA™ 13 mm stents were coated as described in the following:

The PENTA™ stents were coated with a composition containing a 400 μg mixture of high Tg PolyAspirin PX510 and PEG (Mw 18.5K) (PolyAspirin:PEG=9/1 w/w) (Tg mix=10% Tg PEG+90% Tg PA=36.4° C.) in a total concentration of 2% (w/w) in chloroform and then dried at about 80° C. for 45 minutes in an oven. The stents were subject to a crimp test. An SEM image of the coated stent is shown in FIG. 5.

Example 4

PENTA™ 13 mm stents were coated as described in the following:

The PENTA™ stents were primed with a composition containing a 200 μg PolyAspirin (PX261) in a concentration of 2% in chloroform and dried in an oven at 80° C. for 30 minutes. The primed stents were then coated with composition containing a 400 μg mixture of 180 μg PolyAspirin PX510, 20 μg PEG (Mw 18.5K) and 200 μg pactaxel in a total concentration of 2% in chloroform and dried at about 80° C. for 45 minutes in an oven.

Example 5

VISION™ 12 mm stents (available from Guidant Corp.) were coated as described in the following:

VISION™ stents were coated with a composition containing 300 μg poly(ester amide) (Mn=44K, Tg=16° C.) in a concentration of 2% (w/w) in a solvent mixture of dimethylacetamide (DMAC) and methanol (w/w=1:1) and then dried at about 80° C. for 60 minutes in an oven. A coated stent was then tested for wet expansion. As shown in FIG. 6, the coating with PEA has poor mechanical properties.

Example 6

Figure 7:
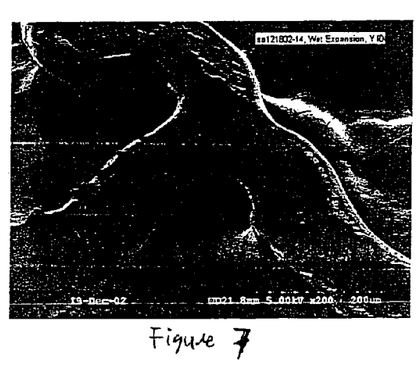
FIG. 7 is a SEM for wet expanded stent coated with 90% PEA mixed with 10% polycaprolactone (PCL) (iv=1.14 dL/g, Tm 60° C.).

VISION™ mm stents were coated as described in the following:

The VISION™ stents were coated with a composition containing a 300 μg mixture of poly(ester amide)) (270 μg, Mn=44K, Tg=16° C.) and polycaprolactone (30 μg, inherent viscosity (i.v.) 1.14 dL/g, Tm 60° C.) in a concentration of 2% (w/w) in a solvent mixture of tetrahydrofuran (THF) (68.6%) and DMAC (29.4%) (total 98%) and then dried at about 80° C. for 60 minutes in an oven. A coated stent was tested for wet expansion. An SEM image shown in FIG. 7 shows some improvements to the stent coating.

Example 7

VISION™ mm stents were coated as described in the following:

The vision stents were coated with a composition containing a 300 μg mixture of poly(ester amide) (210 μg, Mn=44K, Tg=16° C.) and polycaprolactone (90 μg, inherent viscosity (i.v.) 1.14 dL/g, Tm 60° C.) in a concentration of 2% (w/w) in a solvent mixture of tetrahydrofuran (THF) (68.6%) and DMAC (29.4%) (total 98%) and then dried at about 80° C. for 60 minutes in an oven. A coated stent was tested for wet expansion. An SEM image as shown in FIG. 8, shows a much improved coating surface of the stent.

Example 8

PENTA™ 13 mm stents can be coated as described in the following:

Primer: 200 μg high Tg PolyAspirin (PX261), to be coated from a solution of 2% PX261 in chloroform, to be dried 30 minutes at 80° C. in oven;

Load: 400 μg total solid, to be coated from a solution of 1% high Tg PolyAspirin (PX261) and 1.0% Paclitaxel in chloroform, and dried for 45 minutes at 80° C. in oven.

Example 9

PENTA™ 13 mm stents can be coated as described in the following:

Primer: 200 μg high Tg PolyAspirin (PX261), to coated from a solution of 2% PX261 in chloroform, and dried 30 minutes at 80° C. in oven;

Load: 400 μg total solid, to be coated from a solution of 0.95% high Tg PolyAspirin (PX261), 0.05% PEG (18.5K), and 1.0% Paclitaxel in chloroform, and dried for 45 minutes at 80° C. in oven.

Example 10

PENTA™ mm stents can be coated as described in the following:

Primer: 200 μg high Tg PolyAspirin (PX261), can be coated from a solution of 2% PX261 in chloroform, and dried 30 minutes at 80° C. in oven;

Load: 400 μg total solid, can be coated from a solution of 0.90% high Tg PolyAspirin (PX261), 0.10% PEG (18.5K), and 1.0% Paclitaxel in chloroform, and dried for 45 minutes at 80° C. in oven.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of modulating thermal, mechanical, and surface properties of a coating and applying the coating on an implantable device, comprising:
   (1) Providing a first polymer, wherein said first polymer has a glass transition temperature less than or equal to 37° C. and is selected from a poly(ester amide), poly(glycerol sebacic acid), and a low Tg PolyAspirin,
   (2) Reacting said first polymer with a chemical stiffening agent, wherein the agent is an aromatic diol,
   (3) Obtaining a second polymer having a Tg higher than the Tg of the first polymer,
   (4) Forming a coating comprising the second polymer, and
   (5) Applying the coating on an implantable device.

2. The method of claim 1 wherein the coating further comprises a bioactive agent.

3. The method of claim 1 wherein the coating further comprises a bioactive agent selected from the group consisting of zotarolimus, paclitaxel, docetaxel, tacrolimus, pimecrolimus, batimastat, mycophenolic acid, clobetasol, dexamethasone, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl, and combinations thereof.

* * * * *